US012740890B2

(12) United States Patent
Miyashita et al.

(10) Patent No.: US 12,740,890 B2
(45) Date of Patent: Sep. 22, 2026

(54) METHOD FOR MANUFACTURING HEATING BODY, AND HEATING BODY

(71) Applicant: FERRIC INC., Tokyo (JP)

(72) Inventors: Hirokazu Miyashita, Tokyo (JP); Masayoshi Ikezawa, Tokyo (JP); Eiji Miyashita, Tokyo (JP)

(73) Assignee: FERRIC INC., Tokyo (JP)

( * ) Notice: Subject to any disclaimer, the term of this patent is extended or adjusted under 35 U.S.C. 154(b) by 839 days.

(21) Appl. No.: 18/020,356

(22) PCT Filed: Aug. 2, 2021

(86) PCT No.: PCT/JP2021/028647
§ 371 (c)(1),
(2) Date: Feb. 8, 2023

(87) PCT Pub. No.: WO2022/034827
PCT Pub. Date: Feb. 17, 2022

(65) Prior Publication Data

US 2023/0285185 A1 Sep. 14, 2023

(30) Foreign Application Priority Data

Aug. 11, 2020 (JP) ................................ 2020-135953

(51) Int. Cl.
*A61F 7/03* (2006.01)
*B65D 65/38* (2006.01)
(Continued)

(52) U.S. Cl.
CPC .............. *A61F 7/034* (2013.01); *B65D 65/38* (2013.01); *A61F 2007/0098* (2013.01);
(Continued)

(58) Field of Classification Search
CPC ...... A61F 2007/0098; A61F 2007/0223; A61F 2007/038; A61F 7/034; B65D 2565/388; B65D 65/38; F24V 30/00
See application file for complete search history.

(56) References Cited

U.S. PATENT DOCUMENTS 5,918,590 A 7/1999 Burkett et al.
6,436,128 B1 8/2002 Usui
(Continued)

FOREIGN PATENT DOCUMENTS

CA 2404360 A1 9/2001
CN 1407906 A 4/2003
(Continued)

OTHER PUBLICATIONS

Heating element composition, heating element and method for producing the same (Year: 2000).*
(Continued)

*Primary Examiner* — Tigist S Demie
(74) *Attorney, Agent, or Firm* — Osha Bergman Watanabe & Burton LLP

(57) ABSTRACT

Provided is a method for efficiently producing products having good heat generation performance without reducing the production speed by delaying or preventing the start of heat generation of heat-generating compositions/heating elements during production or before sealing to an outer bag. Provided is a production method capable of avoiding unevenness of a heat-generating compositions in a bag/container or formation of a portion not filled with heat-generating compositions. A method for producing a heating element including a heat-generating composition that generates heat upon reaction with oxygen in air includes encapsulating a heat-generating composition precursor including a mixture containing a water-insoluble component of the heat-generating composition in an air-permeable bag/con-
(Continued)

(A)

(B)

(C)

(D)

(E)

tainer formed of a water-permeable packaging material at least in part. The method also includes injecting a liquid component of the heat-generating composition into the heat-generating composition precursor through the water-permeable packaging material from a nozzle tip in contact with the water-permeable packaging material.

15 Claims, 6 Drawing Sheets

(51) Int. Cl.
*A61F 7/00* (2006.01)
*A61F 7/02* (2006.01)

(52) U.S. Cl.
CPC . *A61F 2007/0223* (2013.01); *A61F 2007/038* (2013.01); *B65D 2565/388* (2013.01)

(56) References Cited

U.S. PATENT DOCUMENTS 6,863,682 B2 3/2005 Usui
2002/0151947 A1 10/2002 Usui
2002/0161420 A1 10/2002 Usui
2013/0073016 A1 3/2013 Matsuo
2017/0239085 A1* 8/2017 Miyashita .............. A61H 39/06
2020/0360179 A1 11/2020 Ikezawa et al.

FOREIGN PATENT DOCUMENTS

CN 104024517 A 9/2014
JP S55-59616 U 4/1980
JP H05117640 A 5/1993
JP H09-075388 A 3/1997
JP H10-263002 A 10/1998
JP H11-508786 A 8/1999
JP 2001238906 A * 9/2001
JP 2011-067551 A 4/2011
JP 2012-140537 A 7/2012
WO 2016/063815 A1 4/2016
WO 2019/151472 A1 8/2019

OTHER PUBLICATIONS

International Preliminary Report on Patentability issued in corresponding International Application No. PCT/JP2021/028647 mailed Feb. 23, 2023 (5 pages).
Office Action issued in corresponding Chinese Patent Application No. 202180056575.3, dated Sep. 30, 2025, with translation (18 pages).

* cited by examiner (A)

(B)

METHOD FOR MANUFACTURING HEATING BODY, AND HEATING BODY

TECHNICAL FIELD

The present invention relates to a method for producing a heating element including a heat-generating composition that generates heat upon reaction with oxygen, such as a chemical body warmer, a hot pack structure, or a moxibustion tool; and a heating element.

BACKGROUND ART

A heating element using a heat-generating composition that generates heat upon reaction with oxygen in air is widely used in medical instruments such as a hot pack or a meridian stimulation warming tool, daily necessities such as disposable warmers, and the like.

The heat-generating composition of the heating element to be used in such a warming tool generally includes iron, a salt, activated carbon, water, and, as necessary, other additional components. During production of the heat-generating composition, fine powder of raw materials such as iron powder is likely to fly up and be difficult to handle, and is likely to cause danger due to dust. Thus, water or a salt aqueous solution is added to the other raw materials in an early step. As a typical example, a product such as a disposable warmer is produced by mixing salt water in advance with powder such as iron powder, activated carbon, and the like to produce a mixture of heat-generating composition raw materials, filling the mixture in an air-permeable bag to produce a heating element, and finally sealing the heating element in an airtight outer bag that blocks oxygen.

However, when water is added to a component such as iron powder, an exothermic reaction (oxidation reaction of iron) immediately starts in the presence of oxygen. Thus, in the case of this producing method, the heat generation performance is deteriorated before being sealed in the outer bag. This is particularly significant in the case of using the heat-generating composition in a small amount, such as a heating element to be used as a moxibustion tool. In addition, in the case of producing, by this method, a heating element using a packaging material having high air permeability (for example, a disposable warmer for shoes or a moxibustion tool), water may ooze from the packaging material, or water vapor may pass through the packaging material in a transportation step until encapsulating the produced heating element in the outer bag and dew condensation may occur after encapsulation in the outer bag. From the viewpoint of improving these disadvantages, it is desirable to add water in the latest step possible.

As a method for producing a heating element, there is also known a method in which only a small amount of water is mixed with water-insoluble components such as iron powder, activated carbon, and a water retention material in advance, and a necessary amount of water is further added in a subsequent step (Patent Literature 1). Moreover, there is also a producing method in which a mixture of only water-insoluble components such as iron powder, activated carbon, and a water retention material is molded into a tablet type, filled in a container composed of a packaging material, and then water is injected with a syringe (Patent Literature 2).

Methods as described above may have a certain effect in delaying the start of heat generation occurring during production or before encapsulation in the outer bag, but cause industrial production disadvantages such as an increase in the number of steps and the need to reduce the producing speed. In addition, since the needle hole remains in the packaging material, the method using a syringe cannot be applied to a heating element requiring a packaging material with low air permeability.

Moreover, when the heating element is produced by the conventional method, the bag or container cannot be filled with the heat-generating composition to the full capacity for the purpose of, for example, avoiding a sealing failure due to the heat-generating composition caught in the sealing portion. For this reason, inconveniences occur, such as unevenness of the heat-generating composition in the bag or container, formation of a portion in which the heat-generating composition is not filled in an edge, a corner, or the like of the inner bag or the container, and variation from place to place in heat generation and temperature felt by the user.

CITATION LIST

Patent Literatures

Patent Literature 1: Published Japanese translations of PCT international publication for patent applications JP 11-508786

Patent Literature 2: International Publication WO 2016/063815 A

Patent Literature 3: Japanese Provisional Patent Publication JP 9-75388

SUMMARY OF INVENTION

Technical Problem

An object of the present invention is to solve the problems of conventional methods for producing a heating element as described above, specifically, to provide a method for producing a product having good heat generation performance by delaying or preventing the start of heat generation of a heat-generating composition or a heating element occurring during production or before sealing to an outer bag, and a method for efficiently producing such a product without reducing the production speed.

Moreover, an object of the present invention is to provide a production method capable of avoiding unevenness of a heat-generating composition in a bag or container or formation of a portion not filled with a heat-generating composition, which has occurred when the heating element is produced by the conventional method.

Solution to Problem

According to the present invention, there are provided:

[1]A method for producing a heating element comprising a heat-generating composition that generates heat upon reaction with oxygen in air, the method comprising steps of:

encapsulating a heat-generating composition precursor comprising a mixture containing a water-insoluble component of the heat-generating composition in an air-permeable bag or container at least a part of which is formed of a water-permeable packaging material; and injecting a liquid component of the heat-generating composition into the heat-generating composition precursor through the water-permeable packaging material from a nozzle tip that comes in contact with the water-permeable packaging material;

[2] The method according to the above [1], wherein the water-insoluble component comprises a metallic powder to be oxidized, activated carbon, and a swelling agent;

[3] The method according to the above [1] or [2], wherein the liquid component is water or an aqueous solution containing a salt or one or more water-soluble components;

[4] The method according to any one of the above [1] to [3], wherein the water-permeable packaging material is a packaging material having a water pressure resistance of 30 KPa or less;

[5] The method according to any one of the above [1] to [4], wherein the heat-generating composition precursor further comprises a binder;

[6] The method according to any one of the above [1] to [5], wherein the heat-generating composition precursor is a precursor that expands after injection of the liquid component to a volume 1.1 to 4 times, as compared with a volume before injection of the liquid component;

[7] The method according to any one of the above [1] to [6], wherein the heat-generating composition precursor is in a shaped solid form;

[8] The method according to any one of the above [1] to [7], wherein the water-permeable packaging material is a nonwoven fabric or includes a nonwoven fabric;

[9]A method for producing a heating element comprising a heat-generating composition that generates heat upon reaction with oxygen in air, the method comprising steps of:

encapsulating a heat-generating composition precursor comprising a mixture containing a water-insoluble component of the heat-generating composition in an air-permeable bag or container at least a part of which is formed of a water-permeable packaging material;

injecting a liquid component of the heat-generating composition into the heat-generating composition precursor through the water-permeable packaging material from a nozzle tip that comes in contact with the water-permeable packaging material; and encapsulating the heating element obtained after the step of injecting the liquid component in an airtight outer bag that blocks oxygen; and

[10]A heating element comprising a heat-generating composition that generates heat upon reaction with oxygen in air and an air-permeable bag or container at least a part of which is formed of a water-permeable packaging material and in which the heat-generating composition is encapsulated, wherein the heating element is produced by encapsulating a heat-generating composition precursor comprising a mixture containing a water-insoluble component of the heat-generating composition in the bag or container, and then injecting a liquid component of the heat-generating composition into the heat-generating composition precursor through the water-permeable packaging material.

Advantageous Effects of Invention

According to the present invention, immediately before the heating element is encapsulated in the outer bag, a predetermined amount of liquid can be injected into the heat-generating composition precursor in the packaging material through the packaging material from the outside of the packaging material. Thus, it is possible to prevent deterioration of performance due to heat generation during production of the heating element or before encapsulation in the outer bag. In addition, according to the present invention, since a predetermined amount of liquid can be accurately injected at high speed, a heating element having excellent heat generation performance can be easily and efficiently produced.

Further, according to the present invention, after encapsulation in a bag or container, the heat-generating composition precursor can absorb the liquid and uniformly disperse along or expand to the shape of the bag or container. Thus, without concern of a sealing failure, the heat-generating composition can be uniformly filled into the bag or container without leaving any space. In addition, according to the present invention, it is not necessary to mold the heat-generating composition into the same form as the bag or container in advance, and it is possible to easily and uniformly fill the heat-generating composition even into a bag or container having a complicated shape, which has been conventionally impossible.

1: HEAT-GENERATING COMPOSITION PRECURSOR TABLET, 2: CONTAINER BODY, 3: TOP MEMBER, 4: RECESS, 5: HEAT-GENERATING COMPOSITION.

Figure 3:
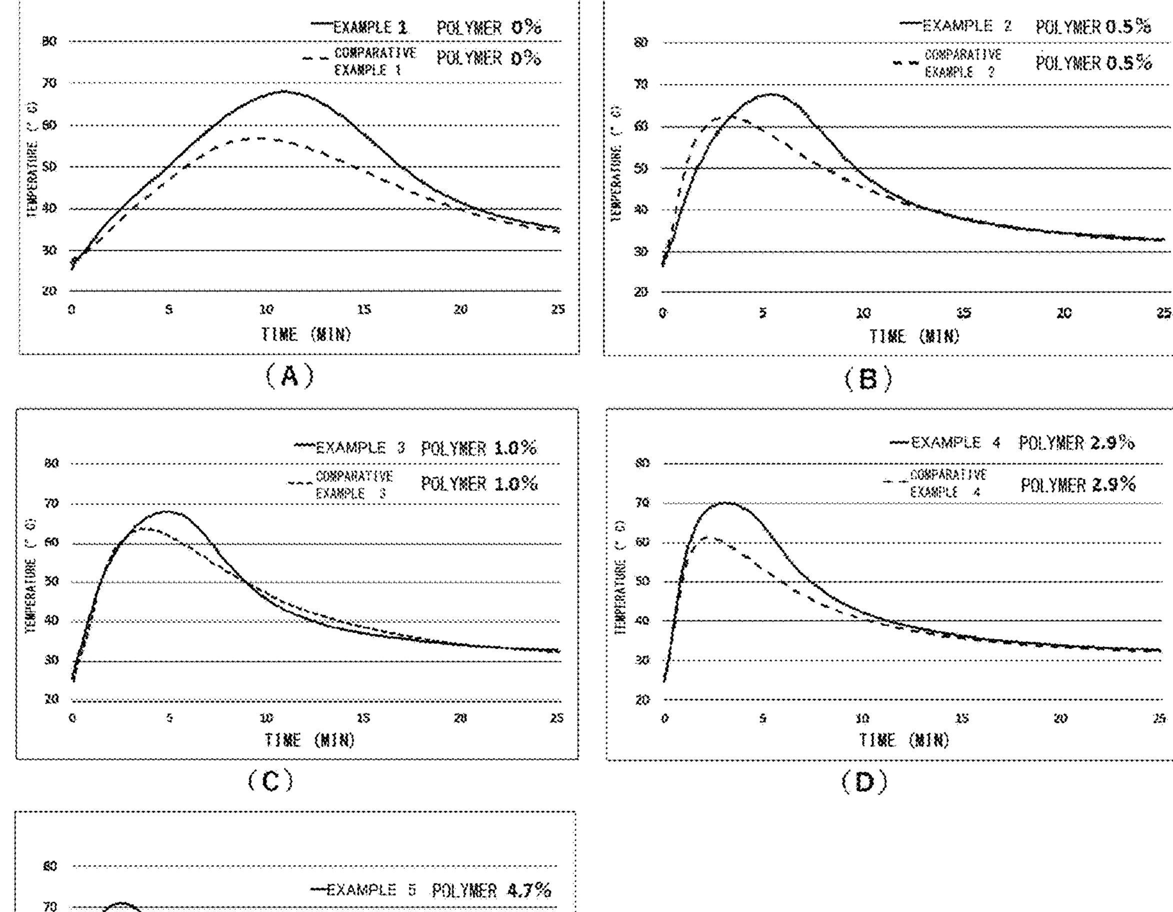

FIG. 3 are diagrams showing heat generation patterns (average of n=3 in all cases) of heating elements of Examples 1 to 5 (solid line) and Comparative Examples 1 to 5 (dotted line). Panel (A) shows Example 1 and Comparative Example 1, Panel (B) shows Example 2 and Comparative Example 2, Panel (C) shows Example 3 and Comparative Example 3, Panel (D) shows Example 4 and Comparative Example 4, and Panel (E) shows Example 5 and Comparative Example 5 for comparison.

Figure 4:
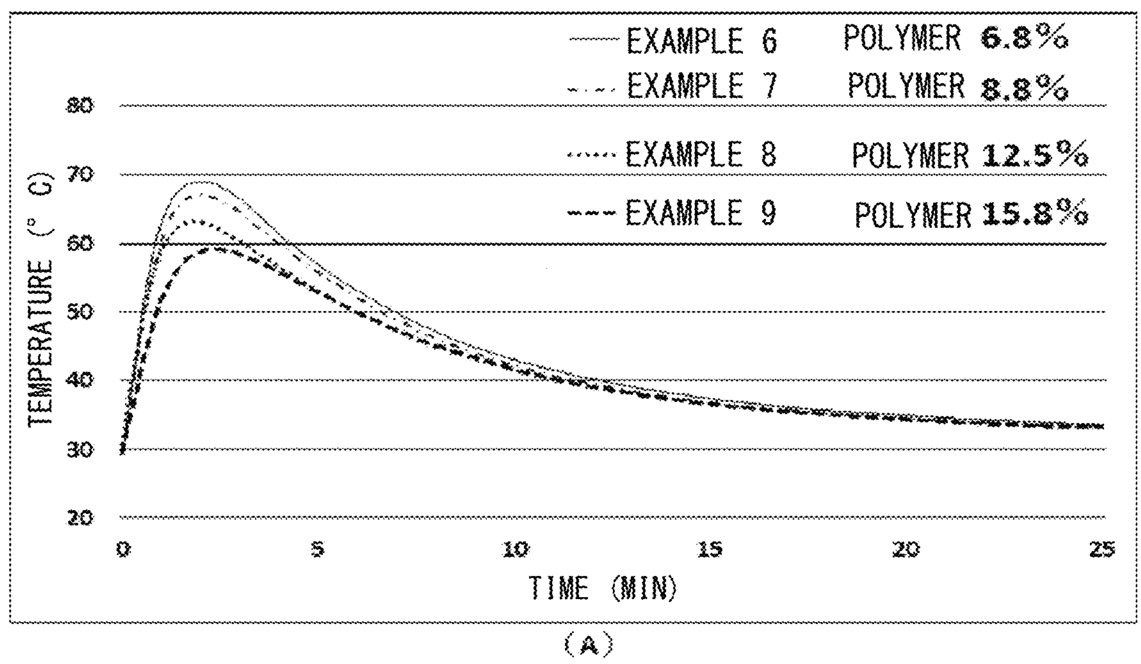
Figure 4:
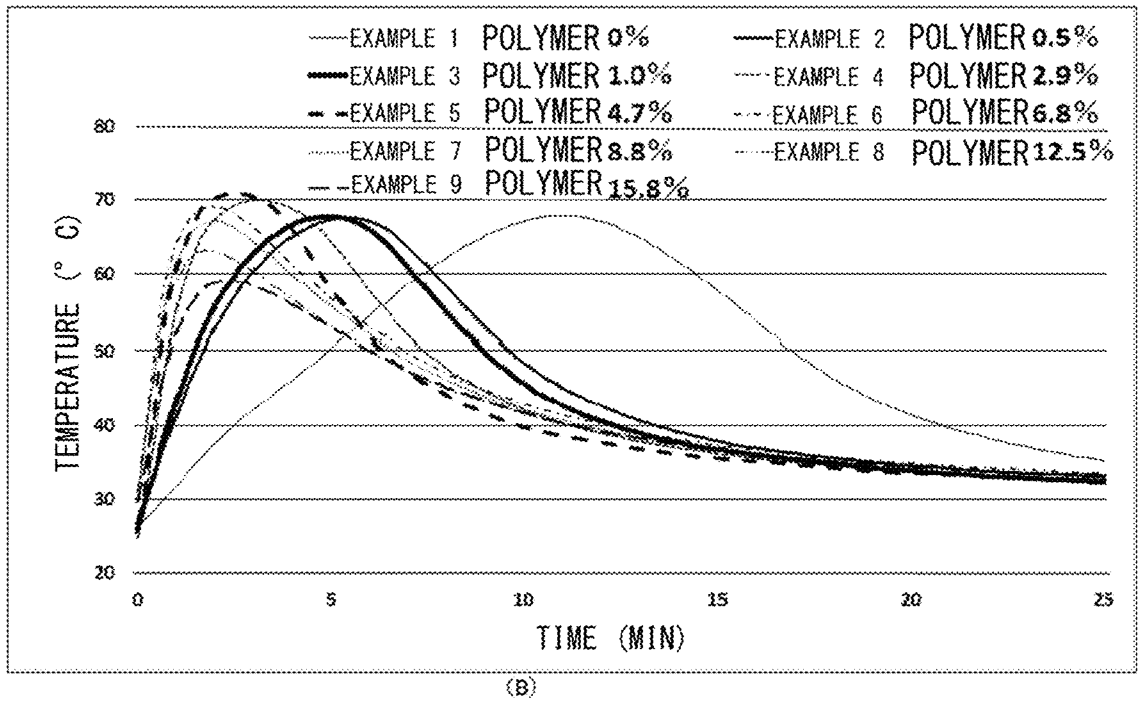

FIG. 4 are diagrams showing heat generation patterns (average of n=3 in all cases) of heating elements of Examples having different contents of the water absorptive polymer. Panel (A) shows heat generation patterns of Examples 6 to 9, and panel (B) shows heat generation patterns of Examples 1 to 9.

Figure 5:
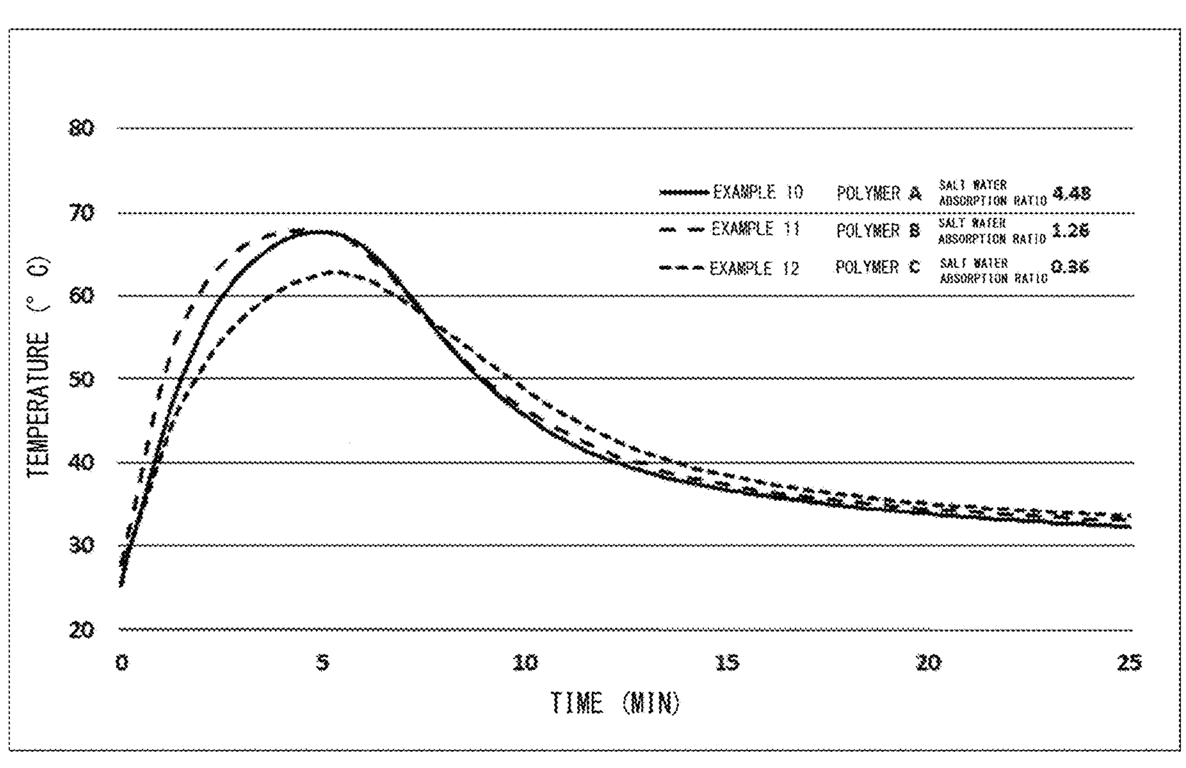

FIG. 5 is a diagram showing heat generation patterns (average of n=3 in all cases) of heating elements of Examples 10 to 12 using water absorptive polymers having different salt water absorption ratios.

Figure 6:
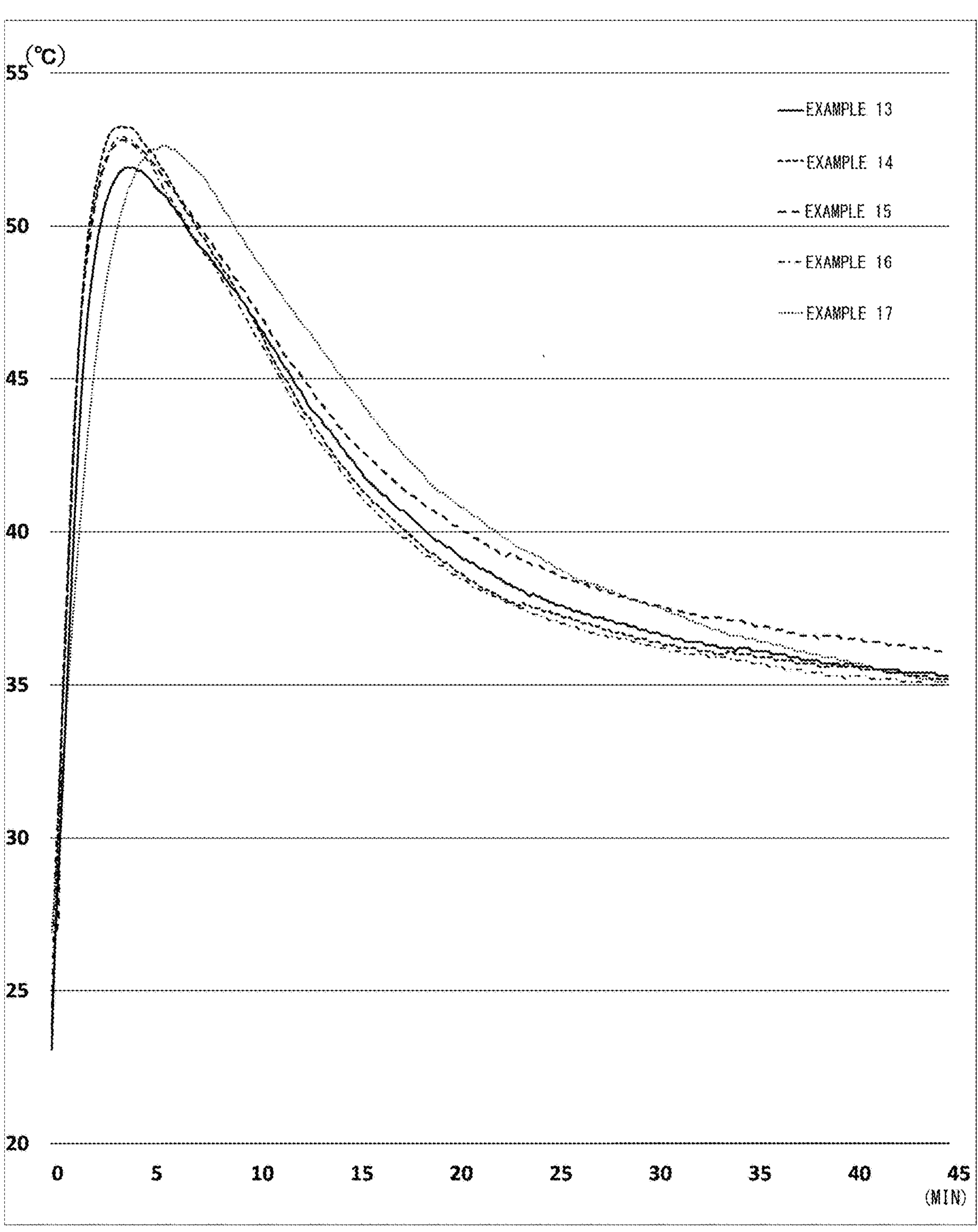

FIG. 6 is a diagram showing heat generation patterns (average of n=3 in all cases) of heating elements of Examples 13 to 17 using packaging materials having different water pressure resistances.

DESCRIPTION OF EMBODIMENTS

Heat-Generating Composition

The heat-generating composition used in the present invention contains a metallic powder to be oxidized, one or more salts, activated carbon, and water. The heat-generating composition contains various additional components described below as necessary.

As the metallic powder to be oxidized, iron powder is generally used, but any metallic powder other than iron powder may be used as long as it generates oxidation heat. For example, iron powder (reduced iron, cast iron, atomized iron, and iron sulfate), aluminum powder, and zinc powder can be used. Typically, the metallic powder to be oxidized is contained in a range from about 10% by weight to about 80% by weight, preferably from about 15% by weight to about 70% by weight when the weight of the heat-generating composition is regarded as 100%. In the present specification, "%" represents "% by weight" unless otherwise specified.

The salt may be any electrolyte as long as it can break down the oxide film formed by oxidation reaction of metal and cause continuous reaction, and salts such as chlorides, sulfates, carbonates, acetates, and nitrates of sodium, potassium, magnesium, calcium, manganese, and copper, or mixtures thereof are generally used. Among these salts, sodium chloride, calcium chloride, magnesium chloride, copper (II) chloride, and mixtures containing them are preferred. Typically, the salt is contained in a range from about 0.5% by weight to about 10% by weight, preferably from about 1% by weight to about 5% by weight when the weight of the heat-generating composition is regarded as 100%.

As the activated carbon, activated carbon derived from a plant-based raw material such as coconut shell or wood is generally used, but activated carbon derived from an animal-based raw material or other raw materials may be used. The activated carbon is typically contained in a range from about 0.5% by weight to about 25% by weight, preferably from about 0.5% by weight to about 20% by weight, and most preferably from about 1% by weight to about 15% by weight when the weight of the heat-generating composition is regarded as 100%.

Water is not particularly limited, and tap water, industrial water, or the like can be used. Typically, the water is contained in a range from about 1% by weight to about 40% by weight, preferably from about 10% by weight to about 30% by weight when the weight of the heat-generating composition is regarded as 100%.

The heat-generating composition used in the present invention preferably further contains a swelling agent. Examples of such a swelling agent include a water absorptive polymer. The swelling agent may be a hydrophilic polymer such as gelatin or agar as long as the swelling agent has a property of expanding the volume by absorbing a liquid, but a hydrophobic polymer that is less likely to be inhibited from swelling by inorganic salts is suitable, and a hydrophobic acrylic acid polymer is particularly preferable. The swelling agent can be from 0 to about 45% by weight and is typically contained in the range of from about 0.1% by weight to about 30% by weight, preferably from about 0.5% by weight to about 20% by weight, and most preferably from about 1% by weight to about 10% by weight, when the weight of the heat-generating composition is regarded as 100%.

In addition, a binder can be contained in order to form the powder raw material into a solid form. Examples of the binder include cellulose (for example, crystalline cellulose), lactose, starch, dextrin, sucrose ester, Teflon (registered trademark), polyethylene glycol, carboxymethyl cellulose, calcium silicate, synthetic hydrotalcite, magnesium aluminometasilicate, dried aluminum hydroxide gel, corn starch, calcium carbonate, gum arabic, gelatin, guar gum, kaolin, dibasic calcium phosphate, tribasic calcium phosphate, polyethylene oxide, xanthan gum, ammonium methacrylate copolymer, vinyl acetate copolymer, syrup, povidone, lactitol, calcium sulfate, and alginic acid. For example, in order to subject the heat-generating composition to tablet molding to form a tablet-type solid, the binder is contained in a range of from 10% by weight to about 30% by weight, preferably from about 10% by weight to about 25% by weight, and most preferably from about 10% by weight to about 20% by weight when the weight of the heat-generating composition is regarded as 100%, so that a tablet having a desired and suitable hardness can be obtained.

Furthermore, a temperature control agent (Patent Literature 2) may be contained. As the temperature control agent, an aliphatic compound having a melting point of 35° C. to 70° C. and having a water solubility at 20° C. of 5 g/100 mL or less, specifically, a higher α-olefin polymer (a copolymer of two or more kinds of α-olefins having 10 to 35 carbon atoms or a copolymer of one or more kinds of α-olefins having 10 to 35 carbon atoms and one or more kinds of other olefins, preferably a side-chain crystallizable polyolefin having a certain long-chain α-olefin at the side chain), various paraffin waxes such as those plant-derived, animal-derived, or petroleum-derived, and the like, myristyl myristate, polyester polyol, polyoxyethylene fatty acid diester, and the like can be used. The temperature control agent can be from 0 to about 40% by weight, and is typically contained in a range from about 0.1% by weight to about 35% by weight, preferably from about 0.5% by weight to about 30% by weight when the weight of the heat-generating composition is regarded as 100%.

In addition, a pH adjuster may be contained to prevent the outer bag from swelling with hydrogen gas during the storage period. Examples of the pH adjuster include sodium sulfite, sodium polyphosphate, and sodium thiosulfate. The pH adjuster is contained in a range from about 0.01% by weight to about 5% by weight, preferably from about 0.1% by weight to about 2% by weight when the weight of the heat-generating composition is regarded as 100%.

As the heat-generating composition of the present invention, those containing a binder are preferable. An example of a particularly preferred formulation is a formulation comprising from 15% by weight to 60% by weight of metallic powder to be oxidized, 1% by weight to 4% by weight of salt, 2% by weight to 10% by weight of activated carbon, 10% by weight to 40% by weight of water, 1% by weight to 10% by weight of swelling agent, 12% by weight to 20% by weight of binder, and 0% by weight to 25% by weight of temperature control agent, when the weight of the heat-generating composition is regarded as 100%.

The heat-generating composition can additionally contain various other components as necessary. Examples of the other additional component include oxidation reaction accelerators, hydrogen gas inhibitors, extenders, fillers, anti-caking agents, thickeners, and surfactants. Specific substances that can be used in the heat-generating composition as these components are known.

Production of Heat-Generating Composition Precursor

The constituent components of the heat-generating composition are divided into components that are solid at normal temperature (hereinafter, sometimes referred to as "solid components") and components that are liquid at normal temperature (hereinafter, sometimes referred to as "liquid components"). The former are further divided into water-insoluble components (a metallic powder to be oxidized, activated carbon, a swelling agent, a temperature control agent, and the like) that are not dissolved in water and water-soluble components (a salt, a pH adjuster, and the like) that are dissolved in water. In the method of the present invention, a heat-generating composition precursor is produced by mixing, among these, only the water-insoluble components or the water-insoluble components and one or more water-soluble components. That is, regarding the present invention, a heat-generating composition precursor refers to a mixture that is composed of components that are solid at normal temperature among the heat-generating composition raw materials, that is composed of water-insoluble components, or that contains water-insoluble components and one or more water-soluble components, and that does not contain a component which is liquid at normal temperature (only water, aqueous solution containing a part or all of the water-soluble components, or an aqueous solution containing a part or all of the water-soluble components and a component which is liquid at normal temperature other than water).

The heat-generating composition precursor can be produced according to a known method by mixing water-insoluble components (and optionally one or more water-soluble components) among the above-described essential components and optional components selected as necessary.

The heat-generating composition precursor may be powder (as mixed powder), but it is preferable to mold the precursor by a known method in order to reduce scattering of dust. For example, the heat-generating composition precursor may be formed by rolling and/or tableting into the form of a disk, a prism, a pyramid, a cube, a cuboid, a cylinder, a cone, an elliptic cylinder, a troche having a hole in the central portion, or the like. A shape having a bottom surface without corners (cylinder, cone, elliptic cylinder, or the like) is preferred. Such a solid-form heat-generating composition precursor is preferable also for eliminating variations in the heat generation temperature because a sealing failure caused by attachment of powder to the sealing portion of a bag or container at the time of encapsulation is avoided, and encapsulation in a predetermined amount can be easily carried out.

The shaped heat-generating composition precursor can have a size and a form depending on the usage of the heating element. For example, in the case of producing a heating element used as a moxibustion tool, the heat-generating composition precursor can be a cylinder form with a diameter of 2 mm to 30 mm and a height of 2 mm to 15 mm.

Bag or Container

The heat-generating composition precursor is filled into a bag or container that is at least partially air-permeable. Thus, a bag or container, or a member thereof, is produced or provided before or after production of the heat-generating composition precursor, or in parallel with the production of the heat-generating composition precursor. Preferably, the bag or container, or a member thereof, is produced in advance or in parallel in order that the heat-generating composition precursor can be encapsulated in the bag or container immediately after being produced.

The shape of the bag or container may be planar (flat) or three-dimensional. According to the present invention, since the heat-generating composition swells in the bag or container so as to match the shape of the bag or container, any shape such as a spherical shape, a three-dimensional shape or a flat shape with many irregularities, or the like can be freely selected.

The components of the heat-generating composition that are liquid at normal temperature are injected from the outside of the bag or container into the bag or container through the packaging material, and absorbed by the heat-generating composition precursor. The bag or container is usually composed of at least two members, one of which is a member having a portion of the bag or container where the liquid component is injected, and one or more of which are not involved in the injection of the liquid component. For example, the former is one surface of the flat bag or the main body of the container, and the latter is the other surface of the flat bag or the top member (lid member) of the container.

The packaging material constituting the portion of the bag or container where the liquid component is injected needs to be a water-permeable packaging material. The packaging material constituting this portion may be an air-permeable packaging material having water permeability. Specifically, the packaging material constituting this portion may be a packaging material having a water pressure resistance lower than water pressure at the time of injection. Considering the relation to the water pressure at the time of injection described later, the water pressure resistance of the packaging material can be, for example, 0.1 to 100 KPa, and is preferably 0.1 to 30 KPa, 0.5 to 30 KPa, or 1 to 30 KPa.

Of the bag or container, the member other than the liquid injection portion in the member having the liquid component injection portion and the member not involved in the injection of the liquid component may be a water-permeable packaging material or a water-impermeable packaging material, and may be an air-permeable packaging material or a non-air-permeable packaging material.

The heat-generating properties of a heating element (rising speed of heat generation, duration of heat generation, thermal conductivity to an object to be heated such as a human body or clothes, and the like) vary depending on the selection of the air-permeable packaging material constituting the bag or container. Therefore, the air-permeable packaging material can be appropriately selected from known materials and used so that the heat-generating properties are in a desired range according to the usage purpose.

An air-permeable packaging material of 10,000 to 40,000 sec/100 cc (JIS P 8117, Gurley method) is used in general body warmers such as those for a human body, and the like, and an air-permeable packaging material of 2,000 to 7,000 sec/100 cc is used in a body warmer for use in shoes. In the case of a heating element, which is designed to be used at high temperature and/or in a short time, such as a meridian stimulation warming tool, a packaging material of 0 to 10,000 sec/100 cc can be used. Accordingly, the air permeability of the air-permeable packaging material constituting the bag or container can be generally 0 to 40,000 sec/100 cc.

The air-permeable packaging material used for the bag or container in the present invention may be a film or sheet entirely or partially having air permeability, and, depending on the purpose, can be appropriately selected according to appropriate necessary heat generation amount, temperature, a heat-generating composition to be used, or the like. Incidentally, as used in the present invention, a "film" mainly indicates a single product (including a single-layered or laminated product; the same applies hereinafter) or a relatively thin product, and a "sheet" mainly indicates a single product, a laminate of two or more single products, or a relatively thick product; however, they are not strictly distinguished.

In the present invention, as an air-permeable film or sheet, a stretched film, preferably, a stretched porous film or a sheet comprising the same is suitably used. The stretched porous film generally contains an inorganic filler and has communication holes formed by stretching so that air permeability is exhibited, and the air permeability can be controlled by controlling this hole diameter or the like.

As a resin constituting a film, generally, a thermoplastic synthetic resin or the like is used. Specifically, polyethylene, polypropylene, polyester, polyamide, polyvinyl alcohol, polyvinyl chloride, polyvinylidene chloride, polyurethane, polystyrene, an ethylene-vinyl acetate copolymer, polycarbonate, or the like is preferably used either alone or in combination.

Such a single-layered or laminated porous film or sheet may be used alone or in combination with a woven fabric or nonwoven fabric, etc. Alternatively, a single-layered or laminated non-porous film or sheet, alone or in combination with a woven fabric or nonwoven fabric, etc., may be provided with needle holes and used. The lamination of the film or sheet can be performed by employing any conventionally known method.

As the water-permeable and/or air-permeable packaging material used for the bag or container in the present invention, the nonwoven fabric is used alone or in combination with a film or a sheet. As a nonwoven, a product conventionally used in the technical field of a heating element, a medical heating tool, or the like is suitably used. For example, the nonwoven fabrics include nonwoven fabrics comprising artificial fibers such as nylon, vinylon, polyester, rayon, acetate, acrylic, polyethylene, polypropylene, and polyvinyl chloride, and natural fibers such as cotton, hemp, silk, and wool; and include nonwoven fabrics in the form such as spunbond, thermal bond, and spunlace. The basis weight of the nonwoven fabric varies depending on the specific gravity of the nonwoven fabric material and bulkiness due to a difference in an entanglement method, and general, it is suitably about 10 g/m$^2$ to about 800 g/m$^2$, with about 20 g/m$^2$ to about 500 g/m$^2$ being particularly preferred. The air permeability measured by JIS P8117 Gurley method is suitably about 0 to 100 sec/100 cc, with about 0 to 50 sec/100 cc being particularly preferred.

The size and form of the bag or container can be arbitrarily selected depending on the usage and the like of the heating element. The solid heat-generating composition precursor molded into a thick form such as a tablet type or a cube type can be contained, for example, in a container having a thickness of about several mm to several cm, instead of the flat bag. In this case, a deep cup of a water-permeable and/or air-permeable packaging material can be formed as the top member (lid) and/or the container main body by a method such as thermoforming or vacuum forming using appropriately packaging materials of various materials as described above.

Figure 2:
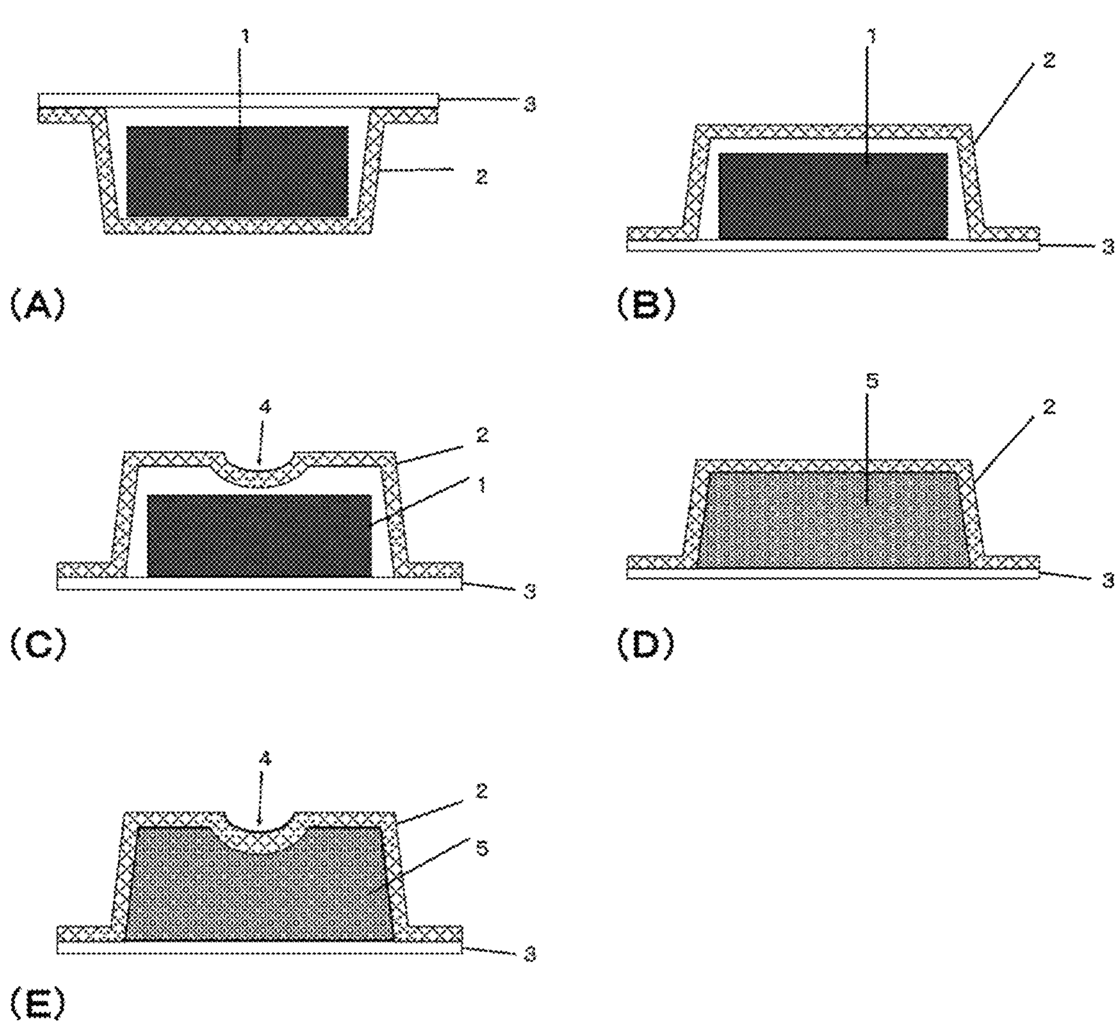
FIG. 2 is a view (cross-sectional view) showing an example of a structure of a meridian stimulation warming tool (moxibustion tool) which is a heating element of the present invention. (A) is a view immediately after encapsulating the heat-generating composition precursor (tablet type) in a container, and (B) and (C) are views after turning upside down for injection of a liquid component (both are before injection of the liquid component). (B) is a container in which a portion for injecting the liquid component is flat, and (C) is a container in which a portion for injecting the liquid component is recessed. Panels (D) and (E) are views illustrating the (B) and (C) after injection of the liquid component, respectively.

Considering the fact that the heat-generating composition precursor (for example, a cylindrical tablet) swells after injection of the liquid component, ease of filling, and the possibility that the liquid component overflows before being absorbed by the heat-generating composition precursor at the time of injection, the diameter and/or the height of the injection surface (upper surface) of the bag or container is preferably slightly larger than the diameter and/or the height of the heat-generating composition precursor tablet (for example, see, Panels (A), (B), and (C) of FIG. 2) because it is better that there is a space (gap between the tablet and the bag or container). In the case of a troche (or donut) shape having a hole in the central portion, since sufficient space can be provided in the portion having the hole, it is not necessary to increase the diameter and/or height of the injection surface (upper surface).

In order to prevent water from leaking from the contact surface between the outer bag and the top surface (injection surface) of the heating element after injection and encapsulation in the outer bag, and/or to prevent water from being blown up after injection, it is preferable to provide a recess in the central portion of the top surface (injection surface) of the heating element (a position corresponding to the position of the nozzle tip) (for example, see, Panel (C) of FIG. 2).

The air-impermeable packaging material can be formed in a single layer or a laminated film or sheet of a resin as described above, and there is no particular limitation on the material, thickness, configuration, and the like as long as the air-impermeable packaging material is suitable for the production of the bag for containing a heat-generating composition.

A separately-produced heat-generating composition precursor is placed in a space formed by each member of a bag or container produced using a packaging material as described above and then the peripheral portions of the member are attached by a method generally used in this technical field, whereby the heat-generating composition precursor can be encapsulated in the bag or container. For example, a heat-generating composition precursor is placed between a member having a portion where a liquid component is injected and a member not involved in injection of the liquid component, and the periphery portions of the layered members are adhered to each other by heat sealing or an adhesive. Alternatively, both members are preliminarily stacked and the periphery portions are adhered to each other by heat sealing or an adhesive while a part of the periphery portions is left open. The heat-generating composition precursor is dispensed into the bag from the opening portion, and then the opening portion is also adhered, whereby the heat-generating composition precursor can be encapsulated.

Injection of Liquid Component

The liquid component of the heat-generating composition is injected into the heat-generating composition precursor encapsulated in the bag or container through the packaging material at the portion of the bag or container where the liquid component is injected. This completes production of the heat-generating composition in the bag or container.

The liquid component may be water or an aqueous solution containing one or more water-soluble components such as a salt aqueous solution, but is preferably water.

The injection of the liquid component can be performed using a machine capable of injecting a predetermined amount. In such a machine, generally, a liquid component is transferred from a container (dish, tank, etc.) containing the liquid component to be injected to a nozzle tip through a flow path, and a predetermined amount of the liquid component is ejected from the nozzle tip of the injection head at a predetermined pressure using a pump or the like. As the pump, a metering pump can be used, and any of reciprocating pumps (plunger pump, piston pump, diaphragm pump, etc.) and rotary pumps (gear pump, screw pump, etc.) can be used. The injection pressure is preferably 1 to 200 KPa.

The cross-sectional shape of the flow path of the liquid component from the injection head inlet to the injection head outlet (that is, the nozzle tip) and/or the shape of the nozzle tip may be any of a circular shape, a shape with corners, and the like. In order to effectively apply pressure to the nozzle tip, the flow path preferably has a diameter of about 0.5 mm to 5 mm in the case of a circular tube, and is an about 0.5 mm to 5 mm square in the case of a square tube.

After injection of the liquid component, the heat-generating composition precursor rapidly absorbs the liquid and expands in the bag or container. This expansion coefficient can be determined by separately calculating or measuring the volume of the heat-generating composition precursor before the liquid injection and the volume of the heat-generating composition precursor after the liquid injection and expansion (at the time when the absorption and expansion of the liquid are stopped) without encapsulating the heat-generating composition precursor in the bag or container, and then comparing them. Since the degree of expansion is affected by the composition of the heat-generating composition, specifically, the amount of liquid to be injected, the content of the swelling agent, the physical properties of the selected substance, and the like, it is possible to adjust the degree of expansion to a desired range by appropriately selecting these. The expansion coefficient is usually about 1.1 times to about 4 times, and is preferably about 1.2 times to about 4 times for filling a bag or container with the heat-generating composition without leaving any space.

In order to accurately inject a predetermined amount of liquid at a high speed, the water-permeable packaging material of the injection portion and the nozzle tip need to be in contact with each other. Thus, the nozzle tip that comes in contact with the water-permeable packaging material of the injection portion is preferably formed of a material having excellent conformability and adhesion for preventing the injection pressure from escaping although the material does not matter. For example, a buffer member made of a flexible or elastic material having a ring shape, a tube shape, or the like may be attached to a tip of a metal tube constituting the flow path. Such a shape of the buffer member may be a bellows shape or a dome shape. Examples of the preferred material of the buffer member include silicon rubber, urethane rubber, and nitrile rubber.

The nozzle tip that comes in contact with the water-permeable packaging material of the injection portion is desirably larger than the cross section of the flow path. In the case of a circular shape, the diameter is preferably about 2 mm to 50 mm. When the diameter increases, droplets after injection by jet accumulate inside or outside the nozzle tip due to surface tension, and there arises a problem that injection accuracy into the heat-generating composition precursor decreases.

Regarding the distance between the heat-generating composition precursor and the water-permeable packaging material of the injection portion, a gap of about 0.5 mm to about 10 mm is preferably present therebetween in consideration of bouncing back of the liquid at the time of injection. However, even if the heat-generating composition precursor and the water-permeable packaging material of the injection portion are in contact with each other at a place where the nozzle tip comes in contact with the packaging material, when there is a gap in the vicinity, water escapes into the gap in the vicinity, so that water can be injected cleanly.

Encapsulation in Outer Bag

After injection of the liquid component, the produced heating element is encapsulated in an outer bag that blocks oxygen, and then stored until the use thereof. Packaging materials and producing methods for such an outer bag are also known. In general, when a heating element is industrially produced in a line, the heating element is transported over several minutes to a step of encapsulating the heating element in an outer bag (packaging machine). After injection of the liquid component, the time until the heating element is encapsulated in the outer bag should be as short as possible, and is preferably within 2 minutes, and more preferably within 1 minute.

Additional Elements of Heating Element

The heating element can be configurated by a bag that is filled with the heat-generating composition produced as described above (for example, a disposable body warmer) or a container that is filled with the heat-generating composition produced as described above (for example, a moxibustion tool). It can further comprise additional elements as necessary. These various elements are known and may be integrated with the bag or container and packaged in an outer bag, or may be provided as separate members to be assembled at the time of use without being enclosed in the outer bag. As examples of the additional elements, there are mentioned various means for fixing the bag or container and various parts to be assembled with the bag or container at the time of use (for example, parts to be used according to the usage of the heating element, such as a container containing a perfume or a medicine and a sheet containing water or a cosmetic material). As examples of the fixing means, there are mentioned an adhesive layer or wet pack layer for pasting the heating element to an object to be heated, a band-shaped member used for fixation by winding the member on an object to be heated, and a mask, support sleeve, or wrist band, which is provided with a pocket for containing a heating element, and the like. Incidentally, regarding the heating element, various agents such as camphor and menthol, or a perfume may be used in combination with a constituent element such as an adhesive layer or a wet pack layer, or a heat-generating composition, and/or a packaging material or a container.

EXAMPLES

1. Production of Heating Element

<Production of Tablet-Type Heat-Generating Composition Precursor>

Iron powder (Powdertech Co., Ltd., reduced iron powder "RDH-3M"), activated carbon (Osaka Gas Chemicals Co., Ltd., wood flour-based activated carbon "Shirasagi S5"), and a salt (Nihonkaisui Co., Ltd., powder salt "EF-300") were used as raw materials that are components in solid form at normal temperature (water-insoluble components and water-soluble components) of the heat-generating composition, a water absorptive polymer (Sanyo Chemical Industries, Ltd., polyacrylic acid-type resin "ST-500D*") was used as a swelling agent, and crystalline cellulose (Asahi Kasei Chemicals Corporation, crystalline cellulose "CEOLUS TG-101") was used as a binder.

For the composition of the heat-generating composition, 45.0% by weight of iron powder, 5.0% by weight of activated carbon, 5.0% by weight of salt, and 20.0% by weight of crystalline cellulose as components that are solid at normal temperature, and 25% by weight of water as a component that is liquid at normal temperature were used as a basic formulation. Various heat-generating compositions shown in Table 1 were designed by appropriately adding a water absorptive polymer thereto.

TABLE 1

| Formulation | Composition of heat-generating composition (%) Iron powder | Activated carbon | Salt | Crystalline cellulose | Water | Water absorptive polymer | Production method Heat-generating component precursor + liquid | Mixed powder of all components |
|---|---|---|---|---|---|---|---|---|
| ① | 45.0 | 5.0 | 5.0 | 20.0 | 25.0 | 0 | Example 1 | Comparative Example 1 |
| ② | 44.7 | 5.0 | 5.0 | 19.9 | 25.0 | 0.5 | Example 2 | Comparative Example 2 |
| ③ | 44.4 | 4.9 | 4.9 | 19.7 | 25.0 | 1.0 | Example 3 | Comparative Example 3 |
| ④ | 43.3 | 4.8 | 4.8 | 19.2 | 25.0 | 2.9 | Example 4 | Comparative Example 4 |
| ⑤ | 42.2 | 4.7 | 4.7 | 18.8 | 25.0 | 4.7 | Example 5 | Comparative Example 5 |
| ⑥ | 41.2 | 4.6 | 4.6 | 18.3 | 25.0 | 6.4 | Example 6 | |
| ⑦ | 39.7 | 4.4 | 4.4 | 17.6 | 25.0 | 8.8 | Example 7 | |
| ⑧ | 37.5 | 4.2 | 4.2 | 16.6 | 25.0 | 12.5 | Example 8 | |
| ⑨ | 35.6 | 3.9 | 3.9 | 15.8 | 25.0 | 15.8 | Example 9 | |

<Production of Heat-Generating Composition Precursor>

The solid component raw materials weighed were enclosed in a polyethylene bag, the mouth was closed with sufficient air, and then the raw materials were mixed for 3 minutes. This mixture of raw materials, 0.75 g, was weighed and tableted using "Desktop Prototype Tableting Machine QUICK MINI FY-TQM-30" by Fuji Yakuhin Kikai Co. Ltd. (tableting pressure, 10 KN). A cylindrical tablet-type heat-generating composition precursor having a diameter of 14 mm and a thickness of 3 mm was produced by using the pressing mold having a diameter of 13.9 mm and the receiving mold having an inner diameter of 14 mm.

<Molding of Container Body>

A polyester spunbond nonwoven fabric (basis weight of 250 g/m$^2$, trade name "ELTAS smash Y15250", Asahi Kasei Corporation) was sandwiched between a convex stainless steel pressing mold and a concave stainless steel receiving mold heated to 110° C., and pressed for 5 seconds to produce a cup-shaped molded product having a diameter of 18 mm and a height of 7 mm. The shape and size of the cup-shaped molded product (member having a portion where a liquid component is injected) are schematically illustrated in Panel (A) of FIG. 1. In this figure, the upper surface is a surface having a portion where a liquid component is injected, and the bottom is opened so as to be closed with a top member after the heat-generating composition precursor is charged.

<Encapsulation in Container>

One tablet-type heat-generating composition precursor was placed in the cup-shaped molded product produced above, and a top member (separator-processed polyester/SIS-based hot-melt adhesive/polyester spunlace nonwoven fabric (basis weight of 30 g/m$^2$)/alumina-deposited polyester/low-density polyethylene) was placed thereon in such a direction that the polyethylene film layer came in contact with the edge of the top of the container main body. Using a stainless steel heat seal bar heated to 180° C., a pressure (10 MPa) was applied from the separator side for 5.5 seconds, and the top member and the container body were thermocompression bonded to encapsulate the heat-generating composition precursor. After encapsulation, the sample was punched out with a Thomson blade to have a diameter of 26 mm.

<Injection of Liquid Component>

In the injection of the liquid component, the product produced above was turned upside down so that the bottom side of the container body is the upper surface, and placed under the nozzle tip of water. Water was supplied at a stroke of 4.5 mm using a "HIBER Pump" manufactured by HIBER with a flow path inlet inner diameter of 2 mm and an outlet inner diameter of 0.8 mm. An edge (nozzle tip) of a silicon buffer member having a diameter of 6 mm attached to the tip of the metal tube of the water injection head was brought into contact with the upper surface (nonwoven fabric surface of the container main body) of the product produced above by encapsulation of the heat-generating composition precursor, and 0.25 g of water was injected per heating element to produce a heating element (Examples 1 to 9).

<Encapsulation in Outer Bag>

Immediately after production, the heating element was encapsulated in an outer bag of 12 μm of transparent alumina vapor-deposited polyester/40 μm of low density polyethylene and left at room temperature.

For comparison, instead of the heat-generating composition precursor, heating elements of Comparative Examples 1 to 5 were produced in the same manner as described above that all the components of the heat-generating composition having the respective compositions shown in Table 1 (including water) were mixed to produce a mixed powder, and 1.0 g of the mixed powder was placed in the same cup-shaped molded product as described above, except the step of injecting a liquid component.

2. Heat Generation Test

The heat generation test was performed according to the method of JIS S4100 "Disposable warmer" and measurement was performed using a heater horizontally placed.

The heat generation test was performed in such a manner that 8 L/min of hot water was circulated in a tank-shaped heater with a size of W 615×D 410×H 60 mm (using a vinyl chloride plate having a thickness of 8 mm) equipped with a water-circulating thermostatic bath and installed in a constant temperature room (room temperature: 20° C., humidity: 65%) to control the surface temperature of the heater (the vinyl chloride plate) to 30° C., and each heating element sample was pasted onto the vinyl chloride plate of the heater surface with the top member faced downward, and a temperature measurement sensor pasted around the center of the bottom surface of the container body with a double-sided tape (temperature measurement machine: Chino Corporation, Graphic recorder KR2S00; sensor: Anritsu Meter Co., Ltd., "ST-22E-005").

The results are shown in FIGS. 3 and 4 and Tables 2 and 3. "Rising" was defined as the time from the start of heat generation to when the temperature reached 40° C. after being taken out of the outer bag, and "duration" was defined as the time from when the temperature reached 40° C. to when the temperature fell below 40° C.

TABLE 2

| | Example 1 | Example 2 | Example 3 | Example 4 | Example 5 | Example 6 | Example 7 | Example 8 | Example 9 |
|---|---|---|---|---|---|---|---|---|---|
| Amount of polymer added | 0% | 0.5% | 1.0% | 2.9% | 4.7% | 6.4% | 8.8% | 12.5% | 15.8% |
| Rising (sec) | 160 | 60 | 50 | 40 | 30 | 20 | 20 | 20 | 30 |
| Maximum temperature (° C.) | 67.9 | 67.6 | 67.7 | 70 | 70.9 | 69.0 | 67.3 | 63.2 | 59.2 |
| Time required to reach (sec) | 650 | 320 | 280 | 190 | 150 | 110 | 110 | 130 | 130 |
| Duration (sec) | 1080 | 740 | 680 | 630 | 560 | 700 | 670 | 650 | 640 |

TABLE 3

| | Comparative Example 1 | Comparative Example 2 | Comparative Example 3 | Comparative Example 4 | Comparative Example 5 |
|---|---|---|---|---|---|
| Amount of polymer added | 0% | 0.5% | 1.0% | 2.9% | 4.7% |
| Rising (sec) | 190 | 30 | 60 | 40 | 30 |
| Maximum temperature (° C.) | 56.8 | 62.5 | 63,7 | 61.4 | 59.4 |
| Time required to reach (sec) | 550 | 150 | 220 | 130 | 120 |
| Duration (sec) | 990 | 630 | 770 | 580 | 590 |

In the case of injecting water into the heat-generating composition precursor at a later time, a maximum temperature of about 60° C. to about 70° C. with a rising time of 60 seconds or less was obtained on the whole except for the case where the water absorptive polymer was not added to the heat-generating composition precursor (Example 1). On the other hand, in the mixed powder containing water, the maximum temperature was about 56° C. to about 63° C., and the maximum temperature tended to be lower than that of the heating element of Examples. When the heat-generating compositions having the same composition were compared with each other, the maximum temperatures of the heating elements of Examples were higher than those of the heating element of Comparative Examples by about 4° C. to about 11° C. for any combination of the contents of the water absorptive polymer. As seen from the above, according to the present invention, heat generation loss occurring during production or before sealing in the outer bag is reduced, and a heating element having good heat generation performance is obtained.

The produced heating element does not change the air permeability (oxygen transmission amount), exhibits the performance of the heating element itself, and is suitable for comparing and determining the heat generation efficiency. The heating element having a rising time of 60 seconds or less and a maximum temperature of 65° C. or higher obviously has better heat generation efficiency than the mixed powder usually used in a warmer.

In these Examples, the maximum temperature was about 65 to 70° C. when 0.5 to 10% by weight of the water absorptive polymer was added, but the maximum temperature tended to decrease when 12.5% by weight or more of the water absorptive polymer was added. This is considered to be because the content of the component involved in heat generation, such as iron powder, relatively decreases as the amount of the water absorptive polymer increases. Thus, it is considered that a desired and suitable maximum temperature can be obtained by adjusting the amounts of other components.

Although the present invention is not limited by a specific mechanism of action, the reason why the heat generation efficiency is improved by the inclusion of the water absorptive polymer is considered to be that an infinite number of cracks are generated by water absorption and swelling of the water absorptive polymer in the heat-generating composition precursor to which the water absorptive polymer is added, and an air inflow path is formed to the central portion of the heat-generating composition. In addition, since it is not completely collapsed, it is considered that the exothermic reaction efficiency is improved due to the distance between iron and activated carbon becoming short.

3. Study of Swelling Agent

<Production of Heating Element>

A heating element was produced basically in the same manner as in the above 1 (Examples 10 to 12). However, as a swelling agent, any one of three kinds of water absorptive polymers, a polyacrylic acid-based resin "ST-500D*" (acrylic acid polymer partial sodium salt crosslinked product, hereinafter, sometimes referred to as "polymer A") manufactured by Sanyo Chemical Industries, Ltd., "OK-100" (acrylic acid polymer partial sodium salt crosslinked product, hereinafter, sometimes referred to as "polymer B") manufactured by Sanyo Chemical Industries, Ltd., and "KI Gel" (Isobutylene/maleic anhydride copolymer, hereinafter, sometimes referred to as "polymer C") manufactured by Kuraray Trading Co., Ltd. was used. In the composition of the heat-generating composition, the components that are solid at normal temperature were 44.4% by weight of iron powder, 4.9% by weight of activated carbon, 4.9% by weight of salt, 19.7% by weight of crystalline cellulose, and 1.0% by weight of a water absorptive polymer, and the component that is liquid at normal temperature was 25% by weight of water.

<Heat Generation Test>

The heat generation test was performed as described in the above 2.

<Measurement of Amount of Salt Water Absorbed under Load>

Figure 1:
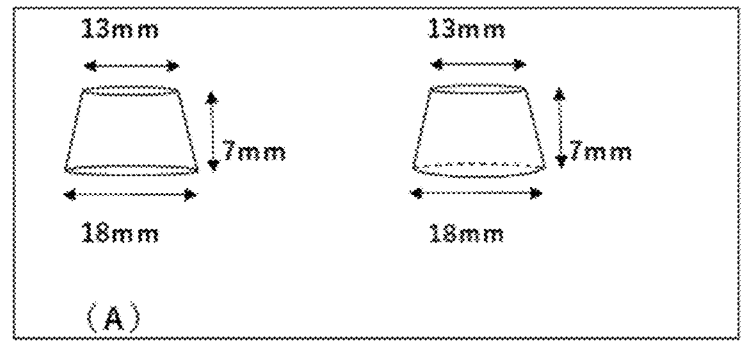
FIG. 1 (A) shows schematic views illustrating a shape (truncated cone shape) and a size of a container main body produced in Examples and Comparative Examples as viewed from a side surface, and FIG. 1 (B) is a schematic view for explaining an apparatus used for measurement of the amount of the salt water absorbed under load.
Figure 1:
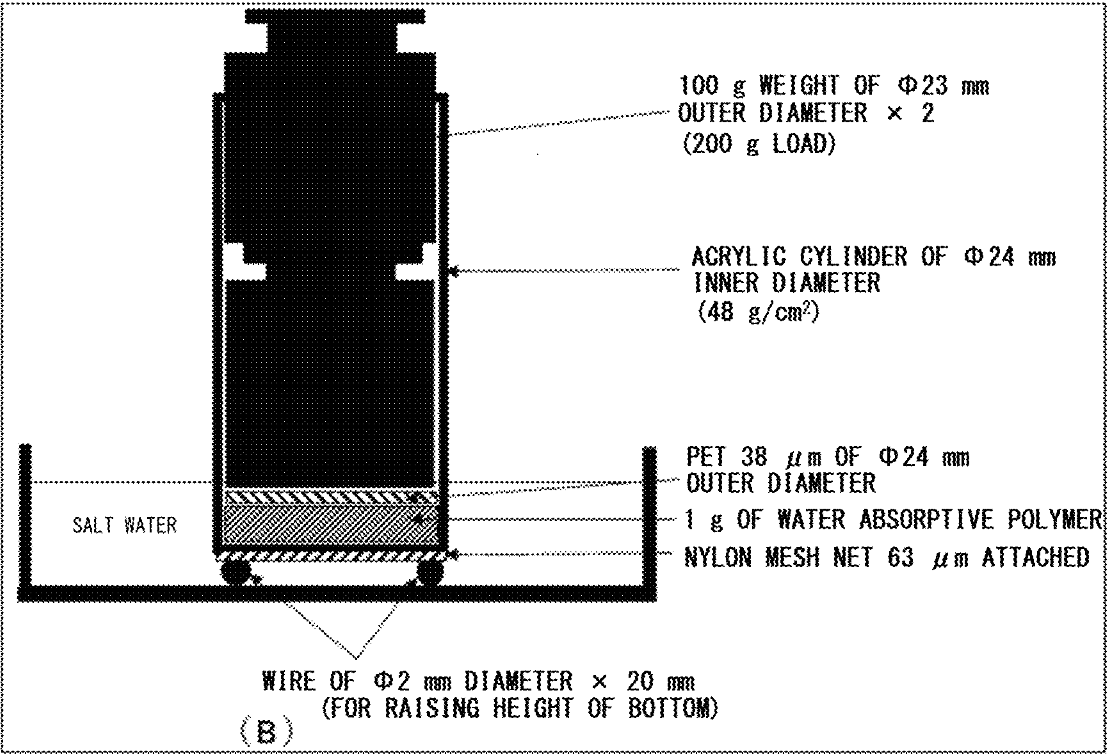

The amount of the salt water absorbed under load was measured at room temperature of 25±1° C. and a liquid temperature of 24±1° C. using the apparatus shown in Panel (B) of FIG. 1, as follows.

An acrylic cylinder (inner diameter of 25 mm, height of 32 mm, and bottom surface with a nylon mesh net 63 μm (N-No. 250HD manufactured by AZUMI FILTER PAPER Co., Ltd.) being attached) was produced, and 1 g of the water absorptive polymer was accurately weighed on the mesh net. On the upper part of the water absorptive polymer, a separator-processed polyester 38 μm having a diameter of 24 mm (one that fits into the plastic cylinder without any gap and smoothly moves up and down) was placed with the separator-processed surface facing the water absorptive polymer side. A cylindrical weight, 200 g (40 g/cm$^2$), was placed on the polyester film to apply a load. A wire (diameter 2 mm) was adhered to a petri dish (inner diameter 85 mm, height 20 mm) containing 8.8 (W/V) % salt water, and the acrylic cylinder prepared above was left on the wire. After being immersed for 2 minutes and taken out, the bottom surface was brought into contact with the quantitative filter paper for 10 seconds to remove excessive moisture. The salt water absorption ratio was determined from the initial weight of the water absorptive polymer and the weight of the water absorptive polymer after absorbing salt water.

Table 4 shows the results of the measurement of the amount of the salt water absorbed under load.

TABLE 4

| | | Apparatus + P | Apparatus | P + Saline | Amount of salt water absorbed | Salt water absorbtion ratio (g/g) | Height of Polymer (mm) |
|---|---|---|---|---|---|---|---|
| Polymer A | ① Initial stage | 6.13 | 5.13 | 1.00 | | | 4 |
| | 2 min immersion 10 sec contact with filter paper | 10.67 | 5.13 | 5.54 | 4.54 | 4.54 | 12 |
| | ② Initial stage | 6.00 | 4.99 | 1.01 | | | |
| | 2 min immersion 10 sec contact with filter paper | 10.60 | 4.99 | 5.61 | 4.60 | 4.55 | 12 |
| | ③ Initial stage | 7.24 | 6.22 | 1.02 | | | |
| | 2 min immersion 10 sec contact with filter paper | 11.67 | 6.22 | 5.45 | 4.43 | 4.34 | 11 |
| | Average | | | | | 4.48 | 12 |
| Polymer B | ① Initial stage | 6.16 | 5.14 | 1.02 | | | 4 |
| | 2 min immersion 10 sec contact with filter paper | 7.43 | 5.14 | 2.29 | 1.27 | 1.25 | 5 |
| | ② Initial stage | 6.81 | 5.81 | 1.00 | | | |
| | 2 min immersion 10 sec contact with filter paper | 8.10 | 5.81 | 2.29 | 1.29 | 1.29 | 5 |
| | ③ Initial stage | 6.15 | 5.15 | 1.00 | | | |
| | 2 min immersion 10 sec contact with filter paper | 7.38 | 5.15 | 2.23 | 1.23 | 1.23 | 4 |
| | Average | | | | | 1.26 | 5 |
| Polymer C | Initial stage | 6.13 | 5.11 | 1.02 | | | 3 |
| | ① 2 min immersion 10 sec contact with filter paper | 6.51 | 5.11 | 1.40 | 0.38 | 0.37 | 4 |
| | ② Initial stage | 6.80 | 5.79 | 1.01 | | | |
| | 2 min immersion 10 sec contact with filter paper | 7.13 | 5.79 | 1.34 | 0.33 | 0.33 | 4 |
| | ③ Initial stage | 5.97 | 4.97 | 1.00 | | | |
| | 2 min immersion 10 sec contact with filter paper | 6.36 | 4.97 | 1.39 | 0.39 | 0.39 | 4 |
| | Average | | | | | 0.36 | 4 |

The results of the heat generation test are shown in Table 5 and FIG. 5.

TABLE 5

| | Example 10 | Example 11 | Example 12 |
|---|---|---|---|
| Salt water absorption ratio under load | 4.48 | 1.26 | 0.36 |
| Rising (sec) | 50 | 40 | 60 |
| Maximum temperature (° C.) | 67.7 | 68 | 62.7 |
| Time required to reach (sec) | 280 | 270 | 310 |
| Duration (sec) | 680 | 720 | 760 |

As seen from the above results, under this condition, the case of using a water absorptive polymer having a salt water absorption ratio under load of 1.0 times or more had a rising time of 60 seconds or less and a maximum temperature of slightly lower than 70° C., and thus was particularly excellent in heat generation efficiency as compared with the case of using a water absorptive polymer having a salt water absorption ratio under load of 0.36 times.

4. Study on Water-Permeable Packaging Material

<Production of Heating Element>

A heating element was produced basically in the same manner as in the above 1 (Examples 13 to 17 and Comparative Examples 6 and 7). The changes are as follows.

As a temperature control agent, an aliphatic compound (α-olefin: Hokoku Corporation, "HS Crysta-6100P") was used. In the composition of the heat-generating composition, the components that are solid at normal temperature were 33.0% by weight of iron powder, 2.6% by weight of activated carbon, 3.7% by weight of water absorptive polymer, 14.7% by weight of crystalline cellulose, 2.6% by weight of salt, and 18.4% by weight of α-olefin copolymer, and the component that is liquid at normal temperature was 25% by weight of water.

As the packaging material of the container main body, the following various packaging materials were used.

Example 13

Polyester spunbond nonwoven fabric (basis weight of 200 $g/m^2$, trade name "ELTAS smash Y15200", Asahi Kasei Corporation), water pressure resistance 9 KPa, air permeability 0.5 sec/100 cc.

Example 14

Polyester spunbond nonwoven fabric (basis weight of 250 $g/m^2$, trade name "ELTAS smash Y15250", Asahi Kasei Corporation), water pressure resistance 8 KPa, air permeability 0.5 sec/100 cc.

Example 15

Polypropylene spunbond nonwoven fabric (basis weight of 200 $g/m^2$, trade name "SPLITOP SP-1200E", MAEDA-KOSEN Co., Ltd.), water pressure resistance 12 KPa, air permeability 0.5 sec/100 cc.

Example 16

High density polyethylene nonwoven fabric (basis weight of 74 $g/m^2$, trade name "Tyvek 1073B", DuPont), water pressure resistance 17 KPa, air permeability 0.5 sec/100 cc.

Example 17

Polyester nonwoven fabric (with water repellent finish) (basis weight of 230 $g/m^2$, trade name "ELTAS smash" Y65230, Asahi Kasei Corporation), water pressure resistance 1 KPa, air permeability 0.5 sec/100 cc.

Comparative Example 6

Polyethylene porous film (basis weight of 40 $g/m^2$, trade name "C5F4040B", Mitsubishi Chemical Corporation), water pressure resistance 250 KPa, air permeability 1,000 (sec/100 cc).

Comparative Example 7

Polyethylene porous film (basis weight of 60 $g/m^2$, trade name "KTF", manufactured by TAI-YOUNG FILM CO., LTD. (太洋製膜股份有限公司), water pressure resistance more than 300 KPa, air permeability 12,000 (sec/100 cc).

In the injection step, 0.4 g of water was injected per heating element as a liquid component. The water pressure at the time of injection was 20 KPa.

In the step of encapsulation in the outer bag, the heating element after the liquid injection was transported to an outer bag packaging machine via a transfer line, and sealed by heat sealing in an outer bag formed of an airtight packaging material (PET 12 m/aluminum foil 7 μm/LLDPE 50 μm, Toho Packaging Inc.). The time from injection of the liquid component to encapsulation was 0.5 minutes.

When the heat-generating composition precursor having the same composition was put into the cup-shaped molded product, next 0.4 g of water was injected, and then the top member was thermocompression bonded or when the mixed powder obtained by mixing all the components including water was encapsulated in the same container, in each case, it took 2.5 minutes to be encapsulated in the outer bag via the transfer line in the same manner.

<Measurement of Water Pressure Resistance of Packaging Material and Injection Amount of Liquid>

The water pressure resistance of the packaging material used for producing the container main body was measured as follows using a water resistance tester manufactured by Toyo Seiki Seisaku-sho, Ltd. in accordance with Chapter 7.1.2 in JIS L 1092 B method (high water pressure method). Water colored in red was prepared by using a dye that does not affect the surface tension of water (72 mN/m), specifically by dissolving 0.5% by weight of "Acid Red" (Red No. 106; CAS No. 3520-42-1) in distilled water.

A test piece of 150 mm square was sandwiched in the order of rubber ring/wire mesh/filter paper/test piece/rubber ring, pressure was increased at a pressure increase rate of 98 KPa/min, and a pressure at which water colored in red started to leak was defined as a water pressure resistance (the measurement portion had a diameter of 100 mm). Although the pressure meter had a pressure value up to 400 KPa, measurement was stopped up to 300 KPa because swinging past the 400 KPa causes a malfunction.

Regarding the injection amount of the liquid, the weight of the heating element (the container and the heat-generating composition precursor) before the liquid injection was measured, and subtracted from the weight of the heating element after the liquid injection to obtain the injection amount. Three specimens were measured for each sample, and the average value was calculated.

The results are shown in Table 6.

TABLE 6

| Packaging material | | Example 13 Polyester nonwoven fabric | Example 14 Polyester nonwoven fabric | Example 15 Polypropylene nonwoven fabric | Example 16 Polyethylene nonwoven fabric | Example 17 Polyester nonwoven fabric (with water repellent finish) | Comparative Example 6 Polyethylene porous film | Comparative Example 7 Polyethylene porous film |
|---|---|---|---|---|---|---|---|---|
| Basis weight (g/m$^2$) | | 200 | 250 | 200 | 74 | 230 | 40 | 60 |
| Water pressure resistance (KPa) | ① | 10 | 6 | 12 | 20 | 1 | 220 | Greater than 300 |
| | ② | 10 | 9 | 12 | 15 | 1 | 230 | Greater than 300 |
| | ③ | 8 | 9 | 11 | 15 | 1 | 300 | Greater than 300 |
| | Average | | 8 | 12 | 17 | 1 | 250 | Greater than 300 |
| Injection amount (g) | ① | 0.40 | 0.39 | 0.41 | 0.41 | 0.41 | 0.00 | 0.00 |
| | ② | 0.41 | 0.41 | 0.42 | 0.42 | 0.40 | 0.00 | 0.00 |
| | ③ | 0.40 | 0.40 | 0.44 | 0.41 | 0.42 | 0.00 | 0.00 |
| | Average | 0.40 | 0.40 | 0.42 | 0.41 | 0.41 | 0.00 | 0.00 |
| Injection condition | | Good Rapidly absorbed | Good Rapidly absorbed | Good Rapidly absorbed | Good Rapidly absorbed | Good Rapidly absorbed | Failure Bounced on surface | Failure Bounced on surface |
| Rising (sec) | | 70 | 60 | 60 | 60 | 90 | — | — |
| Maximum temperature (° C.) | | 51.9 | 53.3 | 52.8 | 52.9 | 52.6 | — | — |
| Duration (sec) | | 1062 | 1008 | 1188 | 978 | 1248 | — | — |

In Examples 13 to 17, since the water-permeable and air-permeable packaging material having a water pressure resistance lower than the water pressure at the time of injection was used, water injected from the outside of the packaging material was accurately absorbed by the heat-generating composition precursor. On the other hand, when an air-permeable packaging material having a high water pressure resistance (low water permeability) was used (Comparative Examples 6 and 7), water did not enter at all, or was not absorbed by the heat-generating composition precursor. Thus, Comparative Examples 6 and 7 could not be used for the heat generating test.

<Heat Generation Test>

The heat generation test was performed as described in the above 2.

The results are shown in FIG. 6.

The heating elements of Examples 13 to 17 exhibited good heat-generating properties. Specifically, the temperature reached 40° C. in about 60 seconds after being taken out from the outer bag, reached the maximum temperature (52 to 53° C.) within 5 minutes, and was able to be maintained at 40° C. or higher for 16 to 20 minutes.

This application is based on Japanese Patent Application No. 2020-135953 filed on Aug. 11, 2020, and the contents described in the specification and claims of Japanese Patent Application No. 2020-135953 are all incorporated herein.

REFERENCE SIGNS LIST

1 Heat-generating composition precursor
2 Container (body)
3 Top member
4 Recess
5 Heat-generating composition

The invention claimed is:

1. A method for producing a heating element comprising a heat-generating composition that generates heat upon reaction with oxygen in air, the method comprising steps of:

encapsulating a heat-generating composition precursor comprising a mixture containing a water-insoluble component of the heat-generating composition in an air-permeable bag or container at least a part of which is formed of a water-permeable packaging material; and injecting a liquid component of the heat-generating composition into the heat-generating composition precursor through the water-permeable packaging material from a nozzle tip that comes in contact with the water-permeable packaging material, wherein:

a gap is formed between the heat-generating composition precursor and an injection surface of the air-permeable bag or container, the nozzle tip is connected to a flow path, and a cross section of the nozzle tip is larger than a cross section of the flow path.

2. The method according to claim 1, wherein the water-insoluble component comprises a metallic powder to be oxidized, activated carbon, and a swelling agent.

3. The method according to claim 2, wherein the liquid component is water or an aqueous solution containing a salt or one or more water-soluble components.

4. The method according to claim 3, wherein the water-permeable packaging material is a packaging material having a water pressure resistance of 30 KPa or less.

5. The method according to claim 4, wherein the heat-generating composition precursor further comprises a binder.

6. The method according to claim 5, wherein the heat-generating composition precursor is a precursor that expands after injection of the liquid component to a volume 1.1 to 4 times, as compared with a volume before injection of the liquid component.

7. The method according to claim 6, wherein the heat-generating composition precursor is in a shaped solid form.

8. The method according to claim 7, wherein the water-permeable packaging material is a nonwoven fabric or includes a nonwoven fabric.

9. The method according to claim 1, wherein the liquid component is water or an aqueous solution containing a salt or one or more water-soluble components.

10. The method according to claim 1, wherein the water-permeable packaging material is a packaging material having a water pressure resistance of 30 KPa or less.

11. The method according to claim 1, wherein the heat-generating composition precursor further comprises a binder.

12. The method according to claim 1, wherein the heat-generating composition precursor is a precursor that expands after injection of the liquid component to a volume 1.1 to 4 times, as compared with a volume before injection of the liquid component.

13. The method according to claim 1, wherein the heat-generating composition precursor is in a shaped solid form.

14. The method according to claim 1, wherein the water-permeable packaging material is a nonwoven fabric or includes a nonwoven fabric.

15. A method for producing a heating element comprising a heat-generating composition that generates heat upon reaction with oxygen in air, the method comprising steps of:

encapsulating a heat-generating composition precursor comprising a mixture containing a water-insoluble component of the heat-generating composition in an air-permeable bag or container at least a part of which is formed of a water-permeable packaging material;

injecting a liquid component of the heat-generating composition into the heat-generating composition precursor through the water-permeable packaging material from a nozzle tip that comes in contact with the water-permeable packaging material; and encapsulating the heating element obtained after the step of injecting the liquid component in an airtight outer bag that blocks oxygen, wherein a gap is formed between the heat-generating composition precursor and an injection surface of the air-permeable bag or container.

* * * * *